(12) United States Patent
Klotz

(10) Patent No.: US 6,647,283 B2
(45) Date of Patent: Nov. 11, 2003

(54) METHOD FOR EXAMINING A LIVING SUBJECT BY NON-INVASIVE IMAGING EMPLOYING A CONTRAST AGENT

(75) Inventor: Ernst Klotz, Uttenreuth (DE)

(73) Assignee: Siemens Aktiengesellschaft, Münich (DE)

( * ) Notice: Subject to any disclaimer, the term of this patent is extended or adjusted under 35 U.S.C. 154(b) by 104 days.

(21) Appl. No.: 10/027,030

(22) Filed: Dec. 20, 2001

(65) Prior Publication Data

US 2002/0151780 A1 Oct. 17, 2002

(30) Foreign Application Priority Data

Dec. 22, 2000 (DE) .......................................... 100 64 768

(51) Int. Cl.⁷ ................................................ A61B 5/05
(52) U.S. Cl. ...................... 600/425; 600/420; 600/431; 600/458; 378/21; 378/45; 378/51; 378/62; 382/131; 382/154
(58) Field of Search ................................. 600/425, 431, 600/420, 458; 378/21–27, 45, 51, 62; 382/131, 154

(56) References Cited

U.S. PATENT DOCUMENTS 6,186,951 B1 * 2/2001 Lizzi et al. .................. 600/458
6,226,352 B1 * 5/2001 Salb ........................... 378/98.9
6,423,007 B2 * 7/2002 Lizzi et al. .................. 600/458

FOREIGN PATENT DOCUMENTS

GB      2 210 533       6/1989
WO      WO 91/12540    8/1991

* cited by examiner

Primary Examiner—Marvin M. Lateef
Assistant Examiner—Jeoyuh Lin
(74) Attorney, Agent, or Firm—Schiff Hardin & Waite (57) ABSTRACT

In a method for examining a living subject with an imaging method making use of the concentration of a contrast agent having a physical property that is identifiable with the imaging method in a region of interest (ROI) of the subject presented in time-successive images acquired with the imaging method representing quantitative values of the physical property, a histogram of the quantitative values of the physical property in the ROI is produced for each of the individual images, and the contrast agent concentration in the ROI is determined on the basis of the frequency of occurrence of the quantitative values of the physical property in the ROI.

13 Claims, 5 Drawing Sheets

METHOD FOR EXAMINING A LIVING SUBJECT BY NON-INVASIVE IMAGING EMPLOYING A CONTRAST AGENT

BACKGROUND OF THE INVENTION

1. Field of the Invention

The present invention is directed to a method for examining a living subject with a non-invasive imaging method including obtaining the time curve of the concentration of a contrast agent having a physical property identifiable with the imaging method in a region of interest (ROI) of the subject presented in time-successive images acquired with the imaging method by identifying quantitative values of the physical property.

2. Description of the Prior Art

Methods of the above type are employed, for example, in x-ray computed tomography in order to be able to start the actual examination given the presence of a specific contrast agent concentration in the ROI.

For this purpose the operator marks, for example, a circular ROI containing the critical anatomical region in a reference image registered without the contrast agent being present, and the time-successive images are registered with the beginning of the administration of contrast agent. The average value of the physical property is determined for each image with respect to the ROI and is compared to the corresponding average of the image registered without the contrast agent. When the average exceeds a threshold that the operator can set, then the actual examination is triggered.

This procedure involves a number of disadvantages.

A first of these is that when the critical anatomical region is small, it is difficult to mark the ROI, moreover the critical anatomical region often cannot be clearly recognized until a certain contrast agent concentration has been reached. Another is that it is difficult under certain circumstances to discern the critical anatomical region only on the basis of anatomical information, for example, tumor-free and vessel-free zones of the liver. Additionally, when the critical anatomical region moves, for example as a consequence of swallowing motions or as a consequence of body movement on the part of the patient, the average of the physical property can be subject to substantial fluctuations, particularly when anatomical structures are located in the proximity of the ROI that exhibit substantial deviations in the value of the physical property from the average of the physical property exhibited the ROI.

SUMMARY OF THE INVENTION

An object of the invention is to provide a method of the type initially described that simplifies the marking of the ROI and is less sensitive to motion.

Thus, in the inventive method, the contrast agent concentration, preferably the time curve of the contrast agent concentration, is not determined on the basis of averages but on the basis of histograms. Differing from the case o observing averages, the increase in the contrast agent concentration in the ROI can be clearly recognized because not only an average but also the frequency of occurrence of the quantitative value of the physical property that corresponds to the contrast agent is identified for the ROI, by means of the histograms. This is even true when the ROI is significantly larger then the critical anatomical region situated within the ROI and wherein the contrast agent accumulates.

Thus, for example, there is the possibility of determining the time curve of the position of a straight line that proceeds parallel to the frequency of occurrence axis of the histogram, and that separates a region of the histogram containing a defined portion of the overall area of the histogram. This determination serves as a criterion for the time curve of the contrast agent concentration. Alternatively, there is also the possibility of determining the time curve of the position of a straight line proceeding parallel to the frequency of occurrence axis of the histogram and through the average of a region of the histogram containing a defined portion of the overall area of the histogram separated by this straight line. This determination also serves as a criterion for the time curve of the contrast agent concentration. In both instances, it is possible to determine the time curve of the contrast agent concentration itself even when the critical anatomical region is practically unrecognizable without the presence of a specific contrast agent concentration, by merely being able to mark a ROI that contains the critical anatomical region. Which of the two said possibilities is preferable in a specific application is dependent on the ratio of the size of the marked ROI to the size of the critical anatomical region, and on the ratio of the expected contrast agent concentration to the noise amplitude.

The defined portion of the overall area of the histogram that is separated corresponds to values of the physical property that lie above the value of the physical property that is dominant given the absence of contrast agent when the value of the physical property belonging to the contrast agent, as is normally the case, lies above the value of the physical property that is dominant given the absence of contrast agent. The defined portion corresponds to values of physical property that lie below the value of the physical property that dominates given the absence of contrast agent when the value of the physical property belonging to the contrast agent lies below the value of the physical property that dominates given absence of contrast agent.

If it is known in advance that no anatomical regions in which a high contrast agent concentration can be anticipated are within the ROI, in a version of the invention that the time curve of the average or median value of a central region of the histogram is determined as a criterion for the contrast agent concentration. This central region is limited by a straight line proceeding parallel to the frequency of occurrence axis of the histogram and separating a region of the histogram containing an upper, defined part of the overall area of the histogram, and by a straight line proceeding parallel to the frequency of occurrence axis of the histogram and separating a region of the histogram containing a lower defined portion of the overall area of the histogram. The upper region containing the defined portion of the overall area of the histogram represents values of the physical property that lie above the values of the physical property corresponding to the middle region of the histogram. The lower region containing the defined portion of the overall area of the histogram represents values of the physical property that lie below the values of the physical property corresponding to the middle region of the histogram.

In a further embodiment of the invention, the determination of the time curve of the contrast concentration can include producing a histogram with respect to an image obtained before the administration of contrast agent, this histogram being compared, for example by subtraction, to the histograms belonging to the time-successive images. The time curve of the spacing between a value of the physical property belonging to the contrast agent and the value of the physical property that dominates in absence of the contrast agent is determined as criterion for the time curve of the contrast agent concentration. The histogram relating to the image produced before the administration of contrast agent can be subtracted from the histograms belonging to the successive images. In this case, the value of the physical property belonging to the contrast agent generates a positive local maximum and the value of the physical property that dominates in the absence of contrast agent generates a negative local maximum in the resultant histogram that is derived by the subtraction. The interpretability of the resultant histogram can be improved when the histogram resulting from the subtraction is convolved with the histogram with respect to the image produced before the administration of contrast agent.

According to a modification of the invention, the time curve of the contrast agent concentration is utilized to start an examination when the central contrast agent concentration exceeds a threshold.

The inventive method is particularly suited for x-ray computed tomography, wherein a substance having very high absorption is usually introduced into the blood circulation as the contrast agent. Substances having a high atomic number, for example iodine (I 53) are frequently employed as the contrast agent.

In order to keep the x-ray dose administered to the patient before the actual examination as low as possible in the case of x-ray computed tomography, a preferred embodiment of the invention the time successive images acquired dependent on quantitative of the physical property are generated with a reduced x-ray dose compared to the x-ray dose employed in the implementation of the actual examination.

The invention is explained below with reference to the example of an exemplary embodiment relating to x-ray computed tomography.

DESCRIPTION OF THE PREFERRED EMBODIMENTS

Figure 1:
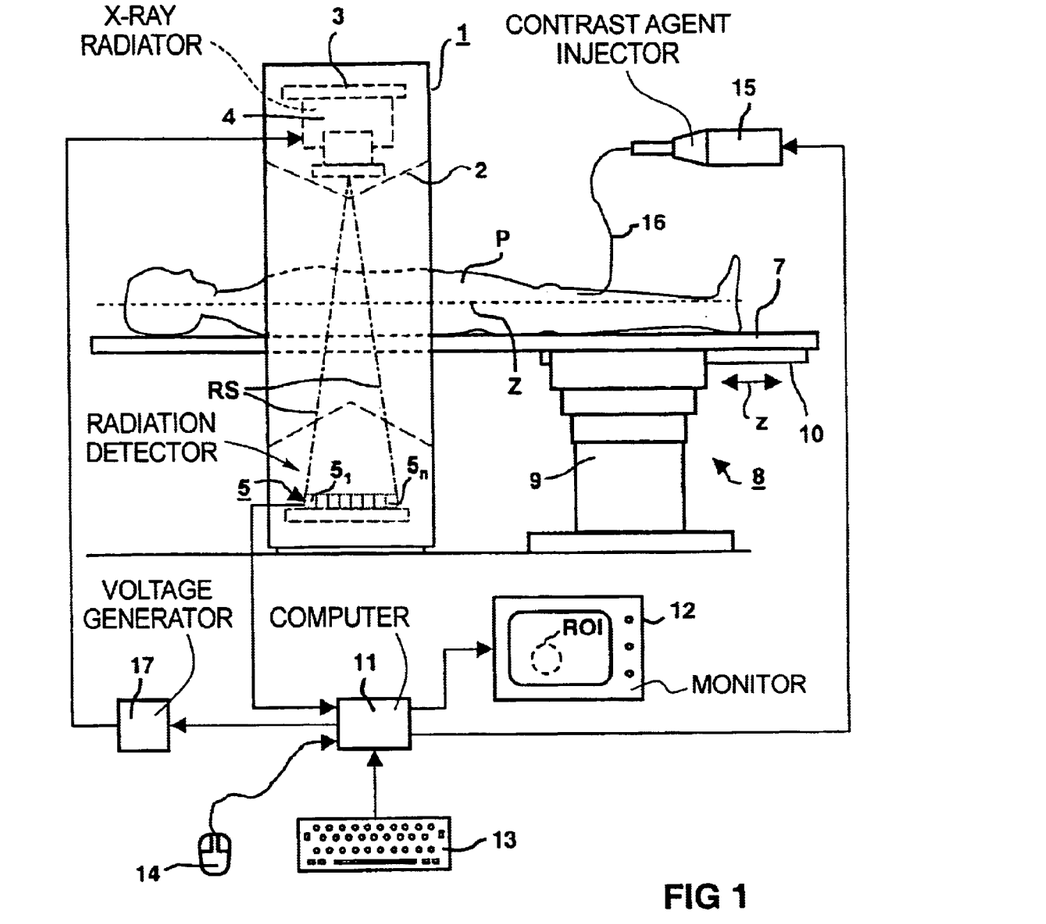
FIG. 1 is a schematic illustration an x-ray diagnostic apparatus, namely an x-ray computed tomography (CT) apparatus operable in accordance with the invention.

FIG. 1 shows an x-ray CT apparatus with a gantry 1 having a measurement opening 2 that is surrounded by a live ring 3 on which an x-ray radiator 4 and a detector system having a detector 5 are mounted. The detector 5 is arcuately fashioned in a known way and is curved around an axis proceeding through the focus of the x-ray radiator 4 and, preferably parallel to a system axis z. The detector 5 has a plurality of lines $5_1$ through $5_n$ of detector elements, each line comprising a row of detector elements. A pyramidal x-ray beam RS that strikes the detector 5 and that is indicated dot-dashed emanates from the x-radiator 4.

The gantry 1 with the x-ray radiator 4 and the detector 5, and at least the support plate 7 provided for the acceptance of an examination subject, for example a patient P, and belonging to a support mechanism 8, are displaceable relative to one another with a motor drive (not shown). These components are displaceable relative to one another in the direction of the longitudinal axis of the support plate 7 proceeding parallel to the system axis Z. In the case of the CT apparatus in FIG. 1, this is achieved by the support plate 7 being displaceably mounted to the base 9 of the support mechanism 8 with a carrier 10, so as to be adjustable in the direction of the system axis Z, i.e. in the direction of the double arrow referenced z.

The support plate 7 is composed of a material that attenuates x-rays only slightly, for example carbon fiber-reinforced plastic (CFK) or wood.

For producing CT exposures, the gantry 1 and the support plate 7 are moved relative to one another into a position wherein the support plate 7 extends through the measurement opening 2 of the gantry 1, and the patient P lying on the support plate 7 assumes a position relative to the gantry 1 such that a region to be examined in the patient P is covered y the x-ray beam RS.

For producing exposures of one or more planar slices of the patient P, the live ring 3 together with the x-ray radiator 4 and the detector 5 is rotated around the system axis Z for registering a number of projections from different directions serving for the reconstruction of one or more tomograms of one or more planar slices of the patient P, the gantry 1 and the support plate 7 retaining their positions relative to one another with respect to the direction of the system axis Z during this rotation. Since the detector 5 has a number of lines $5_1$ to $5_n$ of detector elements, projections with respect to a number of slices of the patient P, corresponding maximally to the number of lines $5_1$ through $5_n$ of the detector 5, can be simultaneously registered. The measured values that correspond to the projections and that derive from one or more lines $5_1$ through $5_n$ of the detector 5 are supplied to a computer 11 that uses these measured values in a known way to calculate a tomogram or a number of tomograms that can be displayed on a display means, for example a monitor 12. A keyboard 13, a mouse 14 and/or further input devices (not shown) for operating the CT apparatus are connected to the computer 11.

For implementation of a spiral scan with the x-ray radiator 4 activated during continuous rotation of the live ring 3, the support plate 7 is displaced on a straight line in the direction of the system axis Z, i.e. in the z-direction, so that the projections that are registered are not planar slices but are one or more helical slices. Using known methods for spiral interpolation, the computer 11 uses the measured projections acquired during the course of the spiral scan to determine calculated projections that refer to one or more desired planar slices and allow the reconstruction of corresponding tomograms. Moreover, it is possible to reconstruct three-dimensional images on the basis of such a spiral scan since not only a planar slice but also a volume that is scanned during the course of a spiral scan.

A contrast agent injector 15 is provided for such examinations, the contrast agent being administered therewith to the patient P via a cannula 16. In the exemplary embodiment, the contrast agent injector 15, as indicated by a control line, is operated by the computer 11, both as to the amount of contrast agent that is administered to the patient P per time unit and as to the beginning and the end of the administration of contrast agent.

The success of examinations implemented with a contrast agent is dependent on the examination not being started until an adequate concentration of the contrast agent is in fact already present in the body region to be examined.

In order to assure this, before the actual examination one or more monitor scans is implemented with a reduced x-ray dose for protecting the patient P, wherein the existing concentration of the contrast agent is initially monitored, and the actual examination that ensues with a normal x-ray dose is triggered only when it can be seen on the basis of the monitor scans that the desired concentration of contrast agent is present.

In order to be able to set the required x-ray dose, a voltage generator 17, that supplies the x-ray radiator 4 with the voltages and currents required for its operation, is likewise controlled by the computer 11, as indicated by a control line.

Figure 2:
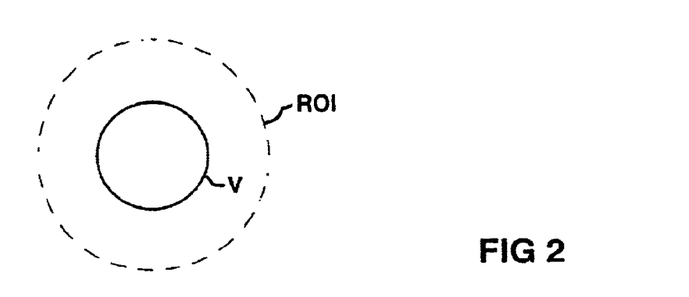
FIG. 2 illustrates the procedure when marking a ROI in the inventive method.

In the inventive method, a monitor scan is first undertaken without activation of the contrast agent injector 15, this monitor scan containing that region of the body of the patient P that is the subject matter of the examination. Using the mouse 14, a ROI, for example a circular ROI indicated with broken lines in FIG. 2 is marked in a tomogram acquired on the basis of the monitor scan implemented without contrast agent and displayed on the monitor 12. The ROI contains the region of the patient—referred to below as the critical region—, for example a blood vessel V visible in cross-section in FIG. 2, such as the carotid artery, wherein the existing concentration of the contrast agent is the determining factor for triggering the actual examination.

After the marking of the ROI has ensued, the contrast agent injector 15 is activated with the operating parameters appropriate for the respective examination, a corresponding actuation of the keyboard 13. Further monitor scans can be implemented after a certain delay time, but these may not be needed dependent on the examination. For each of the tomograms acquired in the course of these monitor scans as well as for the tomogram acquired on the basis of the monitor scan implemented without contrast agent, the computer 11 calculates a histogram of the CT numbers allocated to the picture elements belonging to the marked ROI. These CT numbers, as is known, correspond to the beam attenuation values belonging to the picture elements and being converted into grey scale values in the presentation of the tomograms on the monitor 12.

Taking the frequency of occurrence of the CT numbers in the tomograms into consideration, the computer 11 calculates the existing concentration of contrast agent, at least qualitatively, for example in terms of its time curve, and compares the identified concentration of the contrast agent to a threshold. When this threshold, that can be selected with the keyboard 13 according to the particular examination, is exceeded, the monitor scans are ended and, possibly after a delay time that can be set with the keyboard 13, the actual examination is implemented, either with a stationary or moving support plate 7.

Since, in contrast to known techniques, it is not the average of the CT numbers of the picture elements of the ROI that is utilized as criterion for the contrast middle concentration, but instead the concentration of the contrast agent is determined on the basis of a histogram, it is not necessary, to limit the size of the ROI as closely as possible to the critical region. All that is necessary is to assure that the critical region is in fact located within the ROI and the area of the ROI does not too greatly exceed the area of the critical region, i.e. by no more than five time through twenty-five times dependent on the application.

In an embodiment of the inventive method corresponding to a particular operating mode of the x-ray CT apparatus, the determination of the time curve of the contrast agent concentration is determined by using the position of a straight line proceeding parallel to the frequency of occurrence axis of the histogram, and separating a region of the histogram containing a defined portion of the overall area of the histogram, as a criterion for the time curve of the contrast agent concentration.

Figure 3:
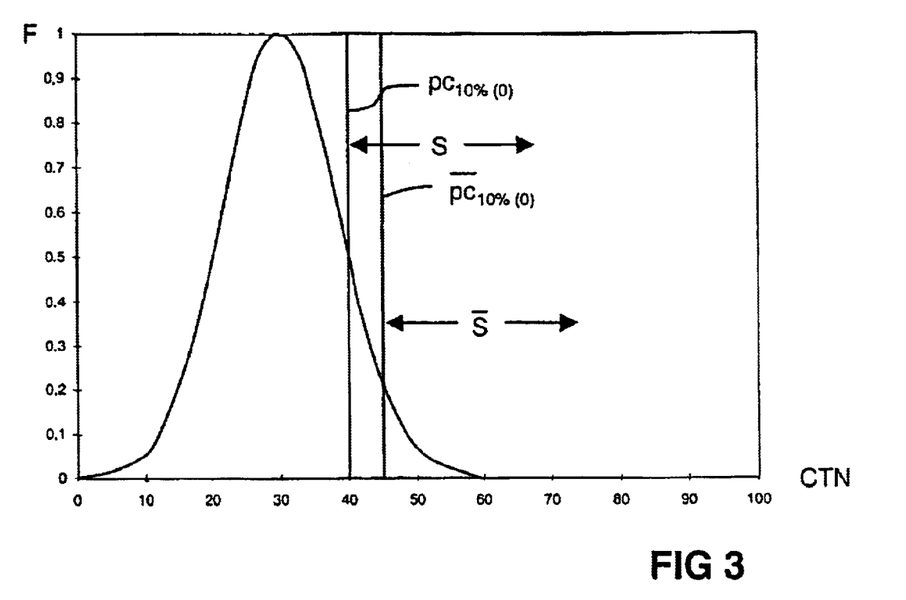
FIGS. 3 through 10 are histograms illustrating operating modes of the x-ray CT apparatus of FIG. 1 in various embodiments of the inventive method.
Figure 4:
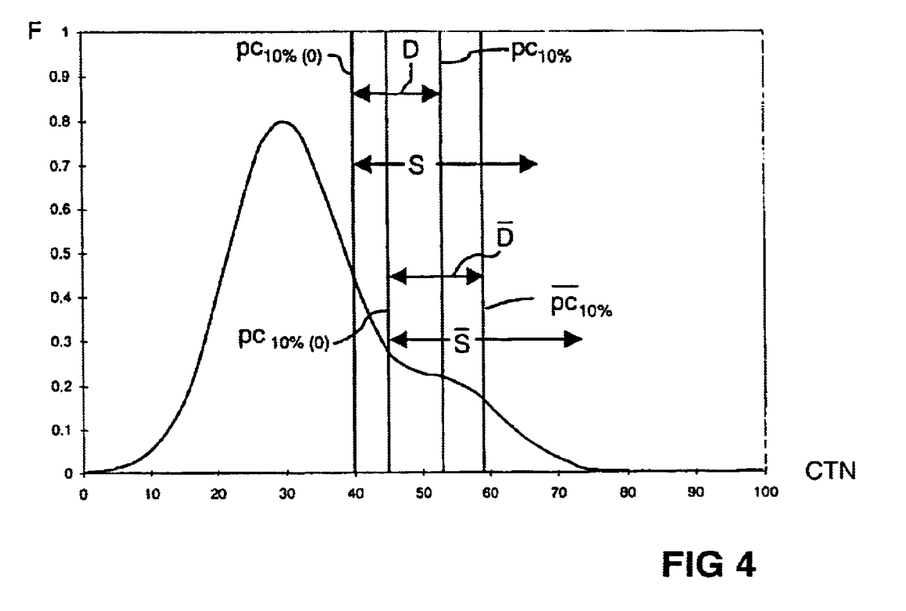
Figure 5:
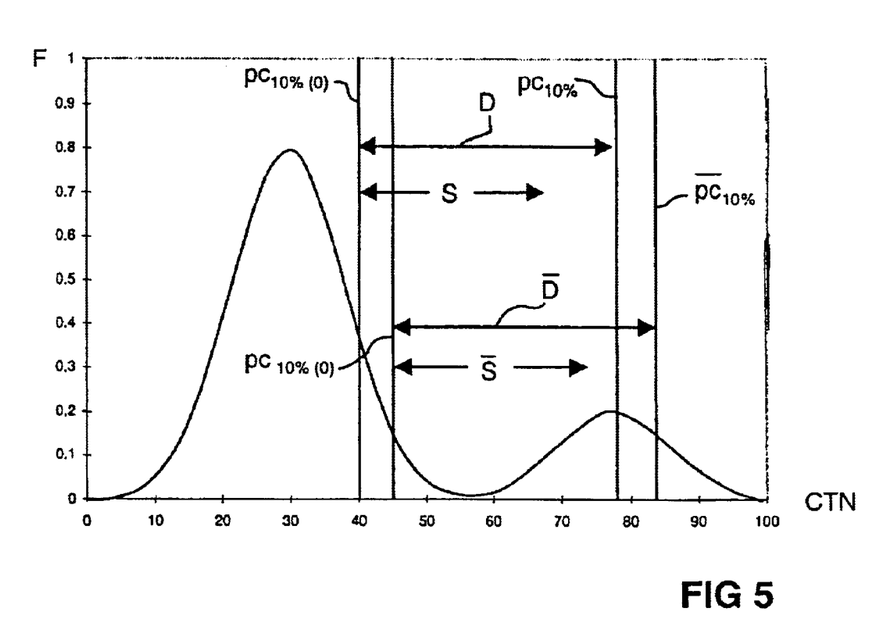

This procedure is illustrated in FIGS. 3 through 5. FIG. 3 shows a histogram that was acquired from a monitor scan before the administration of contrast agent. FIG. 4 shows a histogram that represents the situation of only a relatively slight contrast agent concentration being present in the critical region. The histogram in FIG. 5 represents the situation for a contrast agent concentration in the critical region that is adequate for the implementation of an examination.

The respective CT numbers are entered in the histograms on the horizontal axis referenced CTN and the relative frequencies of occurrence of the CT numbers are entered on the vertical axis referenced F.

When the critical region, as described, is a blood vessel V, the CT number that dominates in the absence of contrast agent, and where the histograms respectively have a maximum, essentially corresponds to the CT number of the tissue surrounding the blood vessel V.

The straight lines in FIGS. 3 through 5 that respectively proceed parallel to the frequency of occurrence axis F of the histogram and separate an exemplary percentage pc of 10% of the overall area of the histogram are respectively referenced $pc_{10\%}$.

The distance D between the straight line $pc_{10\%}$ from the corresponding straight line $pc_{10\%(0)}$ before the beginning of the contrast agent administration is determined as a criterion for the contrast agent concentration respectively present at the time of the individual monitor scans. When this distance D exceeds a threshold referenced S in FIGS. 3 through 5, then the actual examination is triggered, as is in the case of FIG. 5.

As can be seen from FIGS. 3 through 5, the distance D between the straight lines $pc_{10\%(0)}$ and $pc_{10\%}$ represents an unambiguous criterion for the contrast agent concentration that is present in the critical region and, on the basis of the threshold S, enables an exact triggering of the examination, since the part of the histograms defined by the contrast agent is unambiguously identifiable and, in the situation illustrated in FIG. 5, represents a second maximum of the histogram in the region of the CT number corresponding to the contrast agent.

In the case of FIG. 5, moreover, the straight line proceeding parallel to the frequency of occurrence axis and corresponding to the respective percentage pc proceeds through the frequency of occurrence maximum of the histogram corresponding to the contrast agent when the percentage pc in % satisfies the relationship $$pc[\%] = 100\left(1 - \frac{1}{2}\frac{Area_V}{Area_{ROI}}\right)$$

wherein $Area_V$ corresponds to the cross-sectional area of the respective vessel V and $Area_{ROI}$ corresponds to the cross-sectional of the ROI.

Under certain circumstances, it can also be expedient—as additionally illustrated in FIGS. 3 through 5—not to employ the straight line separating a specific percentage of the histogram area, but to employ a straight line proceeding parallel to the frequency of occurrence axis F of the histograms that proceeds through the average of a part of the histogram area corresponding to a defined percentage, such as the part of the histogram area defined by the initially-described straight line proceeding parallel to the frequency of occurrence axis of the histograms. In the case of FIGS. 3 through 5, is the straight line referenced $\overline{pc}_{10\%}$ proceeds through the average of that part of the histogram area separated by the straight line $pc_{10\%}$.

The described procedure is suitable not only for the presentation of vessels but also for brain scans employing contrast agent. In this case, the problem arises that the contrast agent concentration occurring in the brain is very low and the vessel structures are extremely fine, so that they do not normally clearly contrast with the parenchyma in exposures without the contrast agent. In this case, the entire brain is selected as the ROI which, for example, can ensue on the basis of an automatic contour location of the skull. Alternatively, an optimally large region of the brain can be selected as the ROI that contains many arterial structures.

The selection of a defined percentage pc on the same order of magnitude is suitable in view of the blood content in the brain, which amounts to approximately 4% of the cranial volume.

Figure 6:
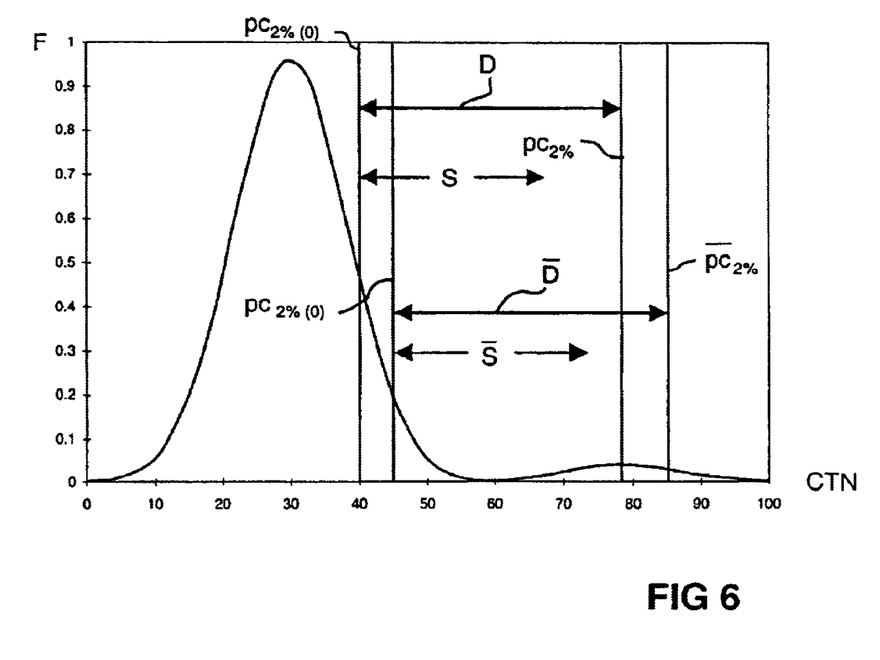

FIG. 6 shows the situation for a defined percentage pc of 2%, from which it is clear that a defined triggering of the actual examination is possible even under these circumstances.

The problem arises in certain examinations of the liver that are conducted for the purpose of locating possible tumors that the triggering of the actual examination must ensue when the normal liver parenchyma is optimally filled with contrast agent. The triggering of the examination is disturbed if the trigger ROI contains either vessels or metastasises that are hard to delimit given the absence of contrast agent.

In an operating mode of the x-ray CT apparatus in a further embodiment of the inventive method, these requirements are satisfied by using the time curve of a middle region of the histogram as the criterion for the time curve of the contrast agent concentration. The middle region of the histogram according to FIG. 7, that shows the situation before the administration of contrast agent, is limited by a straight $pc_{x\%}$ proceeding parallel to the frequency of occurrence axis F of the histogram, and separating a region containing an upper, defined portion of the overall area of the histogram and by a straight line $pc_{y\%}$ proceeding parallel to the frequency of occurrence axis of the histogram and separating a region containing a lower defined portion of the overall area of the histogram.

Figure 7:
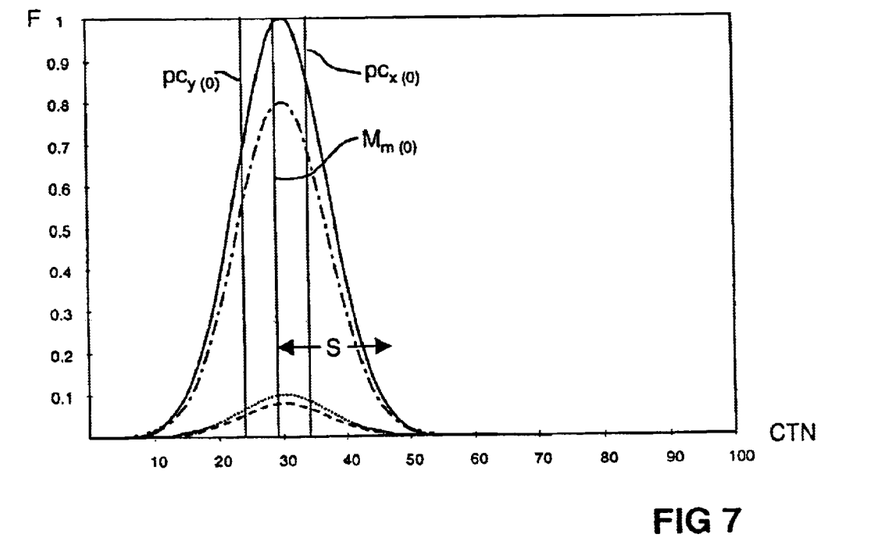

For clear understanding, FIG. 7 shows not only the actual histogram obtained by the monitor scans as a solid line, but also shows a partial histogram for the normal liver parenchyma as a dot-dashed line. The partial histogram for the vessels present in the normal liver parenchyma is indicated as a dotted line and the partial histogram for the metastasises present in the normal liver parenchyma is indicated as a dashed line.

Figure 8:
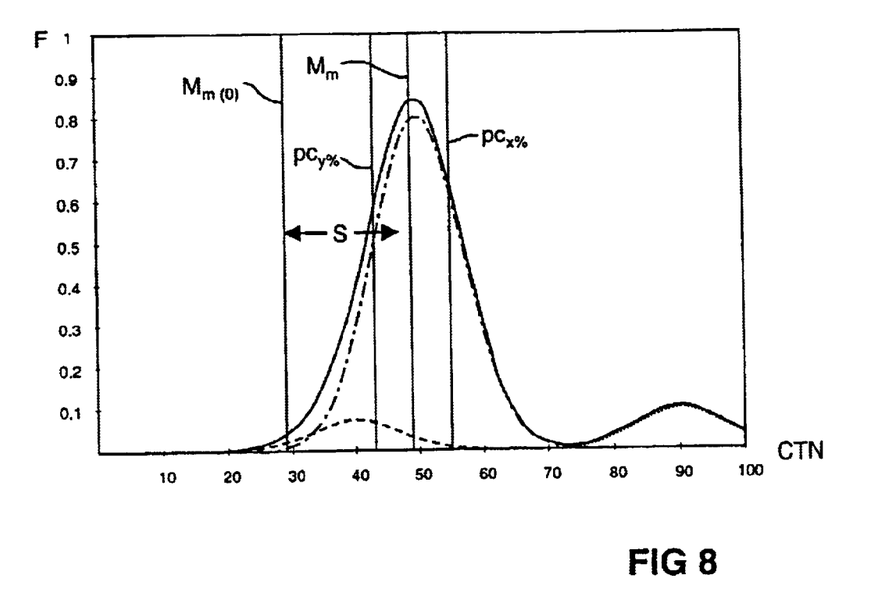

After the administration of contrast agent, the situation illustrated in FIG. 8 exists, wherein the resulting histogram is again shown as a solid line. The partial histograms for vessels and metastasises as well as the normal liver tissue are shown with line types analogous to FIG. 7.

The triggering of the actual examination ensues when the change of the average of the middle region of the histogram, which is illustrated in FIG. 8 by a straight line referenced M that proceeds through the average parallel to the frequency of occurrence axis F, exceeds a threshold S.

It is clear that the triggering of the examination is assured at a time at which the normal liver parenchyma is adequately filled with contrast agent, despite the presence of metastasises and vessels.

When $pc_{x\%}$ and $pc_{y\%}$ lie symmetrically, i.e. $pc_{x\%}=100-pc_{y\%}$, then the change in the median value of the histogram can be employed as the trigger criterion, as a simplification.

In an operating mode of the x-ray CT apparatus in a further embodiment of the inventive method, a histogram is first produced for a monitor scan implemented without contrast agent. Those histograms that result for the monitor scans implemented after the administration of contrast agent are compared thereto, preferably by subtraction.

Figure 9:
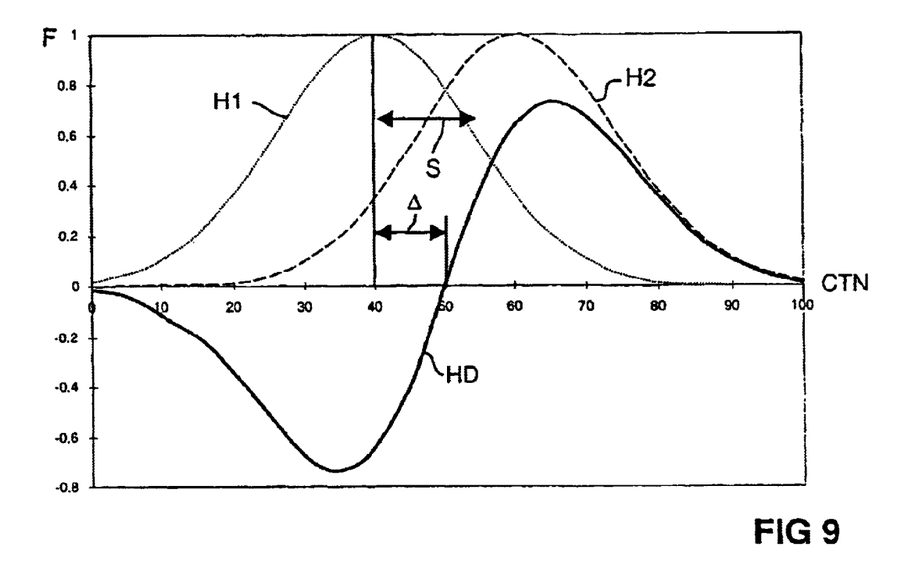

This procedure is illustrated in FIG. 9 on the basis of idealized histograms, whereby the histogram H1 shown dotted was determined on the basis of a monitor scan without contrast agent, whereas the histogram H2 shown dashed is based on a monitor scan implemented sometime after the administration of contrast agent.

A difference histogram HS is formed for the histograms belonging to the individual monitor scans, by taking the difference from the histogram determined without contrast agent administration, with the curve of the difference histogram HS being shown as a solid line in the case of FIG. 9.

The curve of the difference histogram HS exhibits a negative maximum and a positive maximum between which a zero-axis crossing is located. This zero-axis crossing shifts toward higher CT numbers with increasing contrast agent concentration. The zero-axis crossing of the difference histogram HS can be easily identified as a result of the fact that it is situated between the two maxima.

It can be shown that the difference Δ between the CT number corresponding to the zero-axis crossing of the difference histogram HS and the CT number prevailing in the case of the histogram corresponding to the conditions without contrast agent corresponds to the currently existing contrast agent concentration.

The triggering of the actual examination therefore ensues when this difference Δ exceeds a threshold S.

Figure 10:
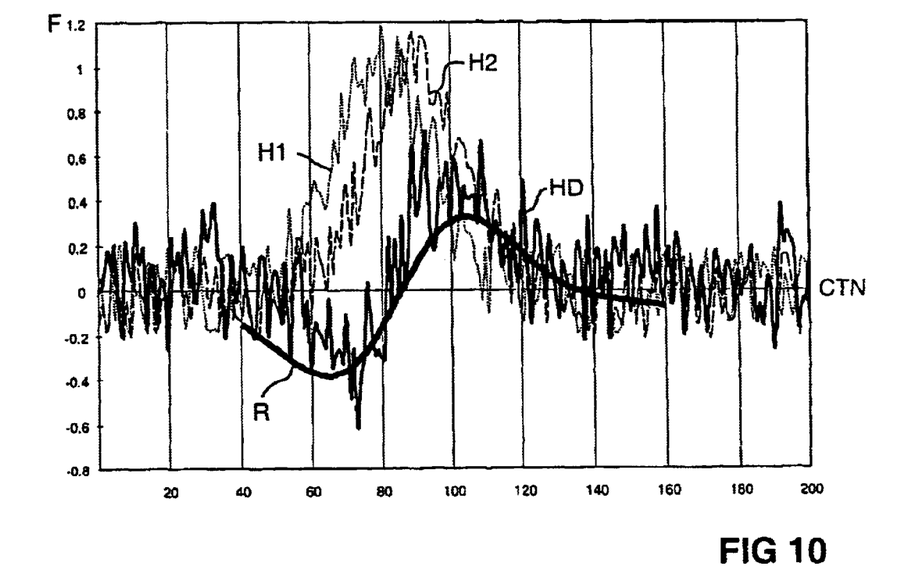

In the inventive method, the x-ray CT apparatus—regardless of the selected operating mode—is operated to implement the monitor scan with an x-ray dose that is reduced compared to the x-ray dose used in the implementation of the actual examination. Due to the increased noise that thereby occurs, the actually identified histograms H1 and H2 deviate, as shown in FIG. 10, from ideal histograms as illustrated in FIG. 9. This is also true of the difference histogram DH whose analysis is thus no longer unambiguously possible, since a number of zero-axis crossings can (and usually will) occur between the positive and negative maxima.

In the described operating mode of the x-ray CT apparatus, the difference histogram DH is therefore convolved with the histogram H1 determined without contrast agent administration, producing the curve shown as a bold-face, solid line in FIG. 10 that, so to speak, corresponds to the smoothed difference histogram HS and can be easily analyzed in the way analogous to FIG. 9.

It should be noted that the determination of the histograms in the individual, above operating modes, the interpretation of the histograms, subtraction and convolution operations, the comparison to thresholds, etc., are implemented by the computer 11.

Likewise, the computer 11 controls the x-ray CT apparatus to generate the sequence of monitor scans and triggers the actual examination given upward transgression of the respective threshold.

The threshold S, just like the position of the straight line $pc_{x\%}$ can be entered into the computer 11 by operating personnel, for example via the keyboard 13. Likewise, the respective operating mode can be selected via the keyboard 13 or with the mouse 14 and the start of the monitor scan thus can be effected.

The inventive method is preferably suited for x-ray diagnostics, particularly computed tomography, but also can be utilized in combination with other non-invasive imaging methods (i.e. imaging methods wherein an examination field is applied at an exterior of the subject) implementable with a contrast agent, for example magnetic resonance and ultrasound.

Although modifications and changes may be suggested by those skilled in the art, it is the intention of the inventor to embody within the patent warranted hereon all changes and modifications as reasonably and properly come within the scope of his contribution to the art.

I claim as my invention:

1. Method for examining a living subject by non-invasive imaging, comprising the steps of:

(a) administering a contrast agent to a living subject;
   (b) obtaining a plurality of successive images, each containing a region of interest of said subject, by non-invasive imaging after administering said contrast agent, said contrast agent having a physical property which is identifiable in said images;
   (c) determining a set of quantitative values of said physical property in each of said images, and generating a histogram, for the region of interest in each of said images of the quantitative values of the physical property in the set for that image, said histogram indicating a frequency of occurrence in the region of interest in of the respective quantitative values in the set; and
   (d) determining a concentration of said contrast agent in said region of interest dependent on said frequency of occurrence in the region of interest in.

2. A method as claimed in claim 1 wherein step (d) comprises identifying a time curve of said concentration as a time curve of the frequency of occurrence of a selected quantitative value in the respective histograms.

3. A method as claimed in claim 2 wherein each of said histograms has a frequency of occurrence axis and a total area, and wherein step (d) comprises, for each histogram, identifying a position of a straight line proceeding parallel to the frequency of occurrence axis which separates a region of the histogram containing a defined portion of said total area, and determining said time curve of said concentration as a time curve of the position of said straight line.

4. A method as claimed in claim 3 wherein step (d) comprises, in a histogram for an image among said plurality of images obtained without contrast agent being present in said region of interest, identifying a reference straight line that proceeds parallel to said frequency of occurrence axis and which separates a region containing a portion, equal to said defined portion, of said total area of the histogram, and identifying the position of the straight line, in respective other histograms, by a distance from said reference straight line.

5. A method as claimed in claim 2 wherein each of said histograms has a frequency of occurrence axis and a total area, and wherein step (d) comprises, for each histogram, designating a region of the histogram containing a defined portion of the total area of the histogram separated by a first straight line proceeding parallel to the frequency of occurrence axis of the histogram, and determining said time curve of said concentration as a time curve of a position of a second straight line proceeding parallel to said frequency of occurrence axis and proceeding through an average value of said designated region.

6. A method as claimed in claim 5 comprising, in a histogram for an image among said plurality of images obtained without contrast agent in said region of interest, identifying a reference straight line proceeding through an average value of a region corresponding to said designated region, and in respective other histograms, determining said position of said second straight line by a distance thereof from said reference straight line.

7. A method as claimed in claim 2, wherein each of said histograms has a frequency of occurrence axis and a total area, and wherein step (d) comprises, in each histogram, designating a central region of the histogram limited by a first straight line proceeding parallel to said frequency of occurrence axis and separating a defined upper portion of said total area of said histogram containing quantitative values of said physical property above quantitative values of said physical property in said central region, and by a second straight line proceeding parallel to said frequency of occurrence axis and separating a region of the histogram containing a defined lower portion of the total area of the histogram containing quantitative values of said physical property below the quantitative values of said physical property in said central region, and identifying a calculated value of the quantitative values of the physical property in said central region of said histogram selected from the group consisting of an average value and a median value, and determining the time curve of the concentration as a time curve of said calculated value.

8. A method as claimed in claim 2 comprising the additional step of obtaining a reference image of said subject, containing said region of interest, in before administering said contrast agent and generating a reference histogram of said region of interest in said reference image, and comparing said reference histogram to the respective histograms for the successive images to obtain, for each comparison, a comparison result, and determining said time curve of said concentration as a time curve of said comparison result.

9. A method as claimed in claim 8 wherein the step of comparing said reference histogram with the respective histograms of said successive images comprises forming a difference between said reference histogram and the respective histograms of the successive images.

10. A method as claimed in claim 9 comprising, for each of said comparisons, obtaining a difference result, and convolving said difference result with said reference histogram.

11. A method as claimed in claim 1 comprising the additional step of beginning a diagnostic examination of said subject when said concentration of said contrast agent, determined in step (d) exceeds a threshold.

12. A method as claimed in claim 1 wherein the step of obtaining a plurality of successive images comprises obtaining said plurality of successive images by computed tomography.

13. A method as claimed in claim 12 comprising the additional step of conducting a diagnostic computed tomography examination of said subject when said concentration of said contrast agent determined in step (d) exceeds a threshold, and further comprising obtaining said plurality of successive images by computed tomography employing an x-ray dose which is less than an x-ray dose employed in said diagnostic computed tomography examination.

* * * * *